United States Patent [19]
Duck et al.

[11] Patent Number: 5,731,146
[45] Date of Patent: Mar. 24, 1998

[54] COMPOSITIONS AND METHODS FOR DETECTING TARGET NUCLEIC ACID SEQUENCES UTILIZING ADJACENT SEQUENCE-ENZYME MOLECULES

[75] Inventors: Peter D. Duck; Faouzi Bekkaoui, both of Burnaby; William L. Crosby, Saskatoon, all of Canada; Richard H. Tullis, Leucadia, Calif.

[73] Assignee: ID Biomedical Corporation, Burnaby, Canada

[21] Appl. No.: 474,624

[22] Filed: Jun. 6, 1995

Related U.S. Application Data

[63] Continuation-in-part of Ser. No. 109,272, Aug. 18, 1993, abandoned.

[51] Int. Cl.$^6$ .............................. C12Q 1/68; C07H 21/04; C07H 21/02; C12N 9/22
[52] U.S. Cl. .............................. 435/6; 435/18; 435/195; 435/199; 514/44; 536/24.3
[58] Field of Search .............................. 435/6, 18, 195, 435/199; 514/44; 536/24.3

[56] References Cited

U.S. PATENT DOCUMENTS

| | | | |
|---|---|---|---|
| 4,839,293 | 6/1989 | Cantor et al. | 435/320 |
| 4,876,187 | 10/1989 | Duck et al. | 435/6 |
| 5,011,769 | 4/1991 | Duck et al. | 435/6 |
| 5,403,711 | 4/1995 | Walder et al. | 435/6 |
| 5,494,814 | 2/1996 | Haseloff et al. | 435/172.3 |

FOREIGN PATENT DOCUMENTS

| | | |
|---|---|---|
| 361 768 A2 | 4/1990 | European Pat. Off. . |
| 361 983 A2 | 4/1990 | European Pat. Off. . |
| 461 731 A2 | 12/1991 | European Pat. Off. . |
| WO 89/10415 | 11/1989 | WIPO . |

OTHER PUBLICATIONS

Corey and Schultz, "Generation of a Hybrid Sequence-Specific Single-Stranded Deoxyribonuclease," *Science* 238: 1401–1403, 1987.

Corey et al., "Sequence-Selective Hydrolysis of Duplex DNA by an Oligonucleotide-Directed Nuclease," *Journal of the American Chemical Society* 111:8523–8525, 1989.

Crouch and Dirksen, "Ribonucleases H," Linn and Roberts (eds.), in *Nucleases*, Cold Spring Harbor Laboratory, Cold Springs Harbor, N.Y., 1982, pp. 211–241.

Dirksen and Crouch, "Selective Inhibition of RNase H by Dextran," *Journal of Biological Chemistry* 256: 11569–11573, 1981.

Duck et al., "Probe Amplifier System Based on Chimeric Cycling Oligonucleotides," *BioTechniques* 9(2):142–147, 1990.

Hostomsky et al., "Ribonucleases H," Linn et al. (eds.), *Nucleases*, 2nd ed., Cold Spring Harbor Laboratory Press, Cold Spring Harbor, N.Y., 1993, Chapter 11, pp. 341–376.

Itaya and Kondo, "Molecular cloning of a ribonuclease H (RNase HI) gene from an extreme thermophile *Thermus thermophilus* HB8: a thermostable RNase H can functionally replace the *Escherichia coli* enzyme in vivo," *Nucleic Acids Research* 19:4443–4449, 1991.

Kanaya et al., "A Hybrid Ribonuclease H. A Novel RNA Cleaving Enzyme with Sequence-Specific Recognition," *Journal of Biological Chemistry* 267:8492–8498, 1992.

Kanaya et al., "Kinetic analyses of DNA-linked ribonucleases H with different sizes of DNA," *FEBS Letters* 354:227–231, 1994.

(List continued on next page.)

*Primary Examiner*—W. Gary Jones
*Assistant Examiner*—Paul B. Tran
*Attorney, Agent, or Firm*—Seed and Berry LLP

[57] ABSTRACT

Briefly stated, the present invention provides novel compositions and methods for detecting target nucleic acid sequences utilizing adjacent sequence-enzyme molecules. Within one aspect of the present invention, oligonucleotide-enzyme fusion molecules are provided, comprising an enzyme capable of cleaving scissile linkages and an oligonucleotide having the structure $(NA_1)_x\!-\!S_z\!-\!(NA_2)_y$ wherein $NA_1$ and $NA_2$ are nucleic acid sequences, S is a scissile nucleic acid linkage, x, y and z are integers from 1 to 100 and n is an integer from 1 to 10.

21 Claims, 9 Drawing Sheets

OTHER PUBLICATIONS

Kanaya et al., "Role of cysteine residues in ribonuclease H from *Escherichia coli*," *Biochem. J.* 271:59–66, 1990.

Kane, C., "Renaturase and Ribonuclease H: A Novel Mechanism That Influences Transcript Displacement by RNA Polymerase II in Vitro," *Biochemistry* 27:3187–3196, 1988.

Sano et al., "A streptavidin–metallothionein chimera that allows specific labeling of biological materials with many different heavy metal ions," *Proc. Natl. Acad. Sci. USA* 89:1534–1538, 1992.

Uchiyama et al., "DNA–Linked RNase H for Site–Selective Cleavage of RNA," *Bioconjugate Chem.* 5:327–332, 1994.

Zuckermann and Schultz, "A Hybrid Sequence–Selective Ribonuclease S," *J. Am. Chem. Soc.* 110:6592–6594, 1988.

Zuckermann and Schultz, "Site–selective cleavage of structured RNA by a staphylococcal nuclease—DNA hybrid," *Proc. Natl. Acad. Sci. USA* 86:1766–1770, 1989.

Zuckermann et al., "Efficient methods for attachment of thiol specific probes to the 3'–ends of synthetic oligodeoxyribonucleotides," *Nucleic Acids Research* 15:5305–5321, 1987.

Kawai et al., Analytical Biochemistry 209:63–69, 1993.

Promega Catalogue, p. 58, 92/93.

Probe Fragment accumulation and detection

| Table 2 | | | | | | | |
|---|---|---|---|---|---|---|---|
| | Target | probe | enzyme | product | CPT coef | Tot CPT coef | ratio |
| | fmoles | fmoles | fmoles | % | | | |
| pIDB9 | 0.01 | 1 | 1 | 0 | 0 | | |
| | 0.1 | 1 | 1 | 0 | 0 | | |
| | 1 | 1 | 1 | 0 | 0 | | |
| pIDB9 | 0.01 | 1 | 50 | 0 | 0 | | |
| | 0.1 | 1 | 50 | 0 | 0 | | |
| | 1 | 1 | 50 | 1 | 0.02 | | |
| pIDB9 | 0.01 | 1 | 5000 | 2 | 0.04 | | |
| | 0.1 | 1 | 5000 | 10 | 0.02 | | |
| | 1 | 1 | 5000 | 60 | 0.01 | 0.092 | |
| pIDB10 | 0.01 | 1 | 1 | 0 | 0 | | |
| | 0.1 | 1 | 1 | 1 | 10 | | |
| | 1 | 1 | 1 | 5 | 5 | | |
| pIDB10 | 0.01 | 1 | 50 | 1 | 2 | | |
| | 0.1 | 1 | 50 | 5 | 1 | | |
| | 1 | 1 | 50 | 55 | 1.1 | | |
| pIDB10 | 0.01 | 1 | 5000 | 5 | 0.1 | | |
| | 0.1 | 1 | 5000 | 50 | 0.1 | | |
| | 1 | 1 | 5000 | 100 | 0.02 | 19.32 | 210 |
| | fmoles | fmoles | fmoles | % | | | |
| ARK2 | 0.01 | 1 | 1 | 0 | 0 | | |
| | 0.1 | 1 | 1 | 0 | 0 | | |
| | 1 | 1 | 1 | 0 | 0 | | |
| ARK2 | 0.01 | 1 | 50 | 0 | 0 | | |
| | 0.1 | 1 | 50 | 10 | 2 | | |
| | 1 | 1 | 50 | 60 | 1.2 | | |
| ARK2 | 0.01 | 1 | 5000 | 70 | 1.4 | | |
| | 0.1 | 1 | 5000 | 90 | 0.18 | | |
| | 1 | 1 | 5000 | 100 | 0.02 | 4.8 | |
| S12 | 0.01 | 1 | 1 | 0 | 0 | | |
| | 0.1 | 1 | 1 | 0 | 0 | | |
| | 1 | 1 | 1 | 5 | 5 | | |
| S12 | 0.01 | 1 | 50 | 5 | 10 | | |
| | 0.1 | 1 | 50 | 40 | 8 | | |
| | 1 | 1 | 50 | 70 | 1.4 | | |
| S12 | 0.01 | 1 | 5000 | 40 | 0.8 | | |
| | 0.1 | 1 | 5000 | 60 | 0.12 | | |
| | 1 | 1 | 5000 | 90 | 0.02 | 25.338 | 5 |

*FIG. 9*

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 8..11
        ( D ) OTHER INFORMATION: /note="Residues 8 to 11 are ribonucleotides"

( x i ) SEQUENCE DESCRIPTION: SEQ ID NO:1:

CATCACCGGA ATTGAAGCC         19

( 2 ) INFORMATION FOR SEQ ID NO:2:

( i ) SEQUENCE CHARACTERISTICS:
        ( A ) LENGTH: 19 base pairs
        ( B ) TYPE: nucleic acid
        ( C ) STRANDEDNESS: unknown
        ( D ) TOPOLOGY: linear ( x i ) SEQUENCE DESCRIPTION: SEQ ID NO:2:

GGCTTCAATT CCGGTGATG         19

( 2 ) INFORMATION FOR SEQ ID NO:3:

( i ) SEQUENCE CHARACTERISTICS:
    ( A ) LENGTH: 28 base pairs
    ( B ) TYPE: nucleic acid
    ( C ) STRANDEDNESS: unknown
    ( D ) TOPOLOGY: linear ( x i ) SEQUENCE DESCRIPTION: SEQ ID NO:3:

TTGCTCGGTG ATGCCCAGCG CCGAATTC                                                28

( 2 ) INFORMATION FOR SEQ ID NO:4:

( i ) SEQUENCE CHARACTERISTICS:
        ( A ) LENGTH: 28 base pairs
        ( B ) TYPE: nucleic acid
        ( C ) STRANDEDNESS: unknown
        ( D ) TOPOLOGY: linear ( x i ) SEQUENCE DESCRIPTION: SEQ ID NO:4:

GAATTCGGCG CTGGGCATCA CCGAGCAA                                                28

( 2 ) INFORMATION FOR SEQ ID NO:5:

( i ) SEQUENCE CHARACTERISTICS:
        ( A ) LENGTH: 30 base pairs
        ( B ) TYPE: nucleic acid
        ( C ) STRANDEDNESS: unknown
        ( D ) TOPOLOGY: linear ( x i ) SEQUENCE DESCRIPTION: SEQ ID NO:5:

CGTCGGGCGC AGCCCACGGG ACGCGGCAGG                                              30

( 2 ) INFORMATION FOR SEQ ID NO:6:

( i ) SEQUENCE CHARACTERISTICS:
        ( A ) LENGTH: 30 base pairs
        ( B ) TYPE: nucleic acid
        ( C ) STRANDEDNESS: unknown
        ( D ) TOPOLOGY: linear ( x i ) SEQUENCE DESCRIPTION: SEQ ID NO:6:

CCTGCCGCGT CCCGTGGGCT GCGCCCGACG                                              30

( 2 ) INFORMATION FOR SEQ ID NO:7:

( i ) SEQUENCE CHARACTERISTICS:
        ( A ) LENGTH: 24 base pairs
        ( B ) TYPE: nucleic acid
        ( C ) STRANDEDNESS: unknown
        ( D ) TOPOLOGY: linear ( x i ) SEQUENCE DESCRIPTION: SEQ ID NO:7:

CCGAATTCTT ATGCCTCTTC GTGA                                                    24

( 2 ) INFORMATION FOR SEQ ID NO:8:

( i ) SEQUENCE CHARACTERISTICS:
        ( A ) LENGTH: 24 base pairs
        ( B ) TYPE: nucleic acid
        ( C ) STRANDEDNESS: unknown
        ( D ) TOPOLOGY: linear ( x i ) SEQUENCE DESCRIPTION: SEQ ID NO:8:

CCGAATTCAA CCCCTCCCCC AGGA                                                    24

( 2 ) INFORMATION FOR SEQ ID NO:9:

( i ) SEQUENCE CHARACTERISTICS:
        ( A ) LENGTH: 23 base pairs

```
            ( B ) TYPE: nucleic acid
            ( C ) STRANDEDNESS: unknown
            ( D ) TOPOLOGY: linear ( x i ) SEQUENCE DESCRIPTION: SEQ ID NO:9:

CCGAATTCCC TCCCCCAGGA AAC                                                        23

( 2 ) INFORMATION FOR SEQ ID NO:10:

( i ) SEQUENCE CHARACTERISTICS:
            ( A ) LENGTH: 24 base pairs
            ( B ) TYPE: nucleic acid
            ( C ) STRANDEDNESS: unknown
            ( D ) TOPOLOGY: linear ( x i ) SEQUENCE DESCRIPTION: SEQ ID NO:10:

CCGCATATGA ACCCTCCCC CAGG                                                        24

( 2 ) INFORMATION FOR SEQ ID NO:11:

( i ) SEQUENCE CHARACTERISTICS:
            ( A ) LENGTH: 30 base pairs
            ( B ) TYPE: nucleic acid
            ( C ) STRANDEDNESS: unknown
            ( D ) TOPOLOGY: linear ( x i ) SEQUENCE DESCRIPTION: SEQ ID NO:11:

AAGGTGAATT CAATGAACCC CTCCCCAGG                                                  30

( 2 ) INFORMATION FOR SEQ ID NO:12:

( i ) SEQUENCE CHARACTERISTICS:
            ( A ) LENGTH: 27 base pairs
            ( B ) TYPE: nucleic acid
            ( C ) STRANDEDNESS: unknown
            ( D ) TOPOLOGY: linear ( x i ) SEQUENCE DESCRIPTION: SEQ ID NO:12:

ACCAAGCTTC TTATGCCTCT TCGTGAA                                                    27

( 2 ) INFORMATION FOR SEQ ID NO:13:

( i ) SEQUENCE CHARACTERISTICS:
            ( A ) LENGTH: 27 base pairs
            ( B ) TYPE: nucleic acid
            ( C ) STRANDEDNESS: single
            ( D ) TOPOLOGY: linear ( i x ) FEATURE:
            ( A ) NAME/KEY: misc_feature
            ( B ) LOCATION: 13..16
            ( D ) OTHER INFORMATION: /note="Residues 13 to 16 are
                ribonucleotides"

( x i ) SEQUENCE DESCRIPTION: SEQ ID NO:13:

GTCGTCAGAC CCAAAACCCC GAGAGGG                                                    27
```

COMPOSITIONS AND METHODS FOR DETECTING TARGET NUCLEIC ACID SEQUENCES UTILIZING ADJACENT SEQUENCE-ENZYME MOLECULES

CROSS-REFERENCE TO RELATED APPLICATIONS

This application is a continuation-in-part of U.S. patent application Ser. No. 08/109,272, filed Aug. 18, 1993, now abandoned; and claims the benefit of PCT Patent Application PCT/CA94/00448, filed Aug. 18, 1994.

TECHNICAL FIELD

The present invention relates generally to methods of detecting a target nucleic acid sequence, and more specifically, to methods for increasing the sensitivity of cycling probe reactions.

BACKGROUND OF THE INVENTION

A wide variety of diagnostic techniques are presently available for detection of organisms within a biological sample, including for example, biochemical tests, immunological tests and cytological tests. The majority of these techniques, however, have drawbacks related to length of time, quantity of sample required, labor training in the use of equipment, expertise level and lack of specificity or sensitivity of detection.

Other techniques which involve direct detection of an organism's nucleic acids have thus been developed in order to address the above-noted concerns. For example, an organism's DNA may be specifically detected by first attaching the DNA to a nitrocellulose filter either directly by bringing it into contact with the filter, or via the Southern transfer technique from an agarose gel. The DNA is then denatured and the filter baked to ensure firm attachment. Generally, this is a time consuming and costly process, which requires a reasonably high level of technical skill.

Next, "probe" DNA is prepared which specifically recognizes, and can bind to, the organism's DNA under appropriate conditions. Briefly, probe DNA is prepared by radioactively labeling specific DNA by nick translation, polynucleotide kinase, or other polymerase type copy reaction using nucleotides labeled with $^{32}$P. Once prepared, the probe DNA is permitted to hybridize with the organism's bound DNA. Hybridization is allowed to proceed at a suitable temperature, typically for several hours. The DNA probe will associate to form hybrid duplexes with any of the bound target DNA that is complementary base sequences. Extraneous material, including unbound probe DNA, is then washed away from the filter and the filter is then exposed to film sensitive to the radioactive label.

One difficulty with such techniques, however, is that biological samples of interest may be limited in terms of the number of cells or quantity of target nucleic acid to be detected, which in turn will affect the sensitivity of the method used. Thus, for successful detection of an organism, target nucleic acids may be increased by various amplification methods in order to overcome the sensitivity limitation of a small number of target organisms.

One of the most widely used in vitro methods for amplifying selected nucleic acid sequences is the polymerase chain reaction (PCR, U.S. Pat. Nos. 4,683,195 and 4,683,202). Briefly, two oligonucleotide primers which flank the DNA segment of the target sequence to be amplified are used to initiate sequential copying of the target sequence. Hybridization of the primers occurs to their complementary sequences on the opposite strands of the target after heat denaturation and replication occurs enzymatically due to DNA synthesis from the two primers. Repetitive cycles of denaturation, followed by primer annealing to target strands and extension is carried out resulting in replication of a complementary strand to each of the original strands per cycle. In turn, each of the product strands is capable of being hybridized to the primers. This results in an exponential amplification of the target nucleic acid followed by detection.

There are a number of technical problems, however, associated with PCR. For example, false positive results can occur from contaminating nucleic acids arising from a number of sources. In particular, PCR products from previous amplification of the target can accumulate in the laboratory, reagents can be easily contaminated and finally, different samples containing high copies of the target can result in cross-contamination. Problems can also arise from the co-amplification of non-specific hybridization of primers to extraneous sequences along the target template. This non-specific amplification increases with each cycle. The technical ability of laboratory personnel, laboratory capabilities and logistics also have to be taken into consideration.

A number of these problems may be resolved if an amplification system other than the target were used. One such method is the cycling probe technology (CPT™, U.S. Pat. Nos. 4,876,187 and 5,011,769), wherein a specific probe containing a scissile linkage, DNA-RNA-DNA oligonucleotide complementary to the target sequence is utilized. In this technology, target nucleic acid molecules are used, through a cyclical RNase H cleavage reaction, to catalyze the conversion of full-length DNA-RNA-DNA probe molecules to shorter probe fragments which can then be detected in a variety of ways.

The present invention discloses novel methods for detecting target nucleic acid sequences, which are simple, rapid and inexpensive to use. The methods provided herein may be accomplished at a constant temperature, and thus do not require thermocycling. Moreover, production of the probe fragments is extremely rapid, linear and easily quantifiable, and since the target is not amplified there is no danger of sample cross-contamination.

SUMMARY OF THE INVENTION

Briefly stated, the present invention provides novel compositions and methods for detecting target nucleic acid sequences utilizing adjacent sequence-enzyme molecules. Within one aspect of the present invention, methods are provided for detecting a target nucleic acid wherein a target nucleic acid molecule, a complementary single-stranded nucleic acid probe having a scissile linkage, and a first complementary adjacent sequence-enzyme molecule (also referred to as "flanking sequence-enzyme molecule") are reacted under conditions which allow the probe and adjacent sequence-enzyme molecule to hybridize to the target nucleic acid, thereby forming a double-stranded, target-probe-adjacent sequence complex. Within this method, the adjacent sequence-enzyme molecule is capable of cleaving the probe portion of the target-probe-adjacent sequence complex at the scissile linkage, so that one or more portions of the nucleic acid probe are released from the target-probe-adjacent sequence complex. The released portions of the nucleic acid probe may then be detected, thus allowing determination of the presence of the target nucleic acid. Within a further aspect, the methods further comprise the step of reacting the target nucleic acid molecule, complementary single-stranded nucleic acid probe having a scissile linkage, and first complementary adjacent sequence-enzyme molecule with a second adjacent sequence-enzyme molecule, the second adjacent sequence-enzyme molecule being complementary to the target nucleic acid molecule and being positioned at an opposing end of the probe as compared to the first adjacent sequence.

Within another aspect of the present invention, methods are provided for detecting a target nucleic acid comprising the steps of (a) reacting a target nucleic acid molecule and a complementary single-stranded nucleic acid probe having a scissile linkage and an attached enzyme molecule under conditions which allow the target nucleic acid and probe to hybridize to each other and form a double-stranded, target-probe complex, wherein the enzyme molecule is capable of cleaving the probe of the target-probe complex at the scissile linkage, such that one or more portions of the nucleic acid probe are released from the target-probe-adjacent sequence complex, and (b) detecting the released portions of the nucleic acid probe, and thereby determining the presence of the target nucleic acid.

Within various embodiments of the above methods, such methods further comprise the step of repeating step (a) such that additional portions of a nucleic acid probe are released from a target-probe-adjacent sequence complex. Yet other embodiments of the invention are described in more detail below, as well as set forth in the figures.

Within additional embodiments of the invention, the nucleic acid probe having a scissile linkage has the structure $[(NA_1)_x (—S—)_z (—NA_2)_y]_n$ wherein $NA_1$ and $NA_2$ are nucleic acid sequences (composed of nucleic acids or nucleic acid analogues), —S— is a scissile linkage and x, y, and z are integers from 1–100 and n is an integer from 1–10. Within one embodiment, the scissile nucleic acid linkage is an RNA sequence. Within another embodiment, the enzyme is a ribonuclease such as RNase H. Within yet other embodiments, the probe is immobilized on a solid support.

Within another aspect of the present invention, oligonucleotide-enzyme molecules are provided comprising an enzyme capable of cleaving scissile linkages, and a nucleic acid molecule (composed of nucleic acids or nucleic acid analogues). Within various embodiments, the enzyme portion of the oligonucleotide-enzyme molecule is a ribonuclease such as RNase H. Within other embodiments, the oligonucleotide is linked to the enzyme molecule by a biotin-streptavidin linkage. Within yet other embodiments, the oligonucleotide molecule is covalently linked to the enzyme molecule. Within a preferred embodiment, the oligonucleotide-enzyme molecule contains a scissile linkage. Within a particularly preferred embodiment, the oligonucleotide-enzyme molecule has the structure $[(NA_1)_x (—S—)_z (—NA_2)_y]_n$ wherein $NA_1$ and $NA_2$ are nucleic acid sequences (composed of nucleic acids or nucleic acid analogues), —S— is a scissile linkage and x, y, and z are integers from 1–100 and n is an integer from 1–10. Within a further embodiment, $NA_1$ and $NA_2$ are DNA molecules, and —S— is an RNA molecule.

Within other embodiments of the invention, oligonucleotide-enzyme molecules are provided which are linked or joined together by a linker of the structure $L_n$, wherein L is a monomeric (e.g., carbon atom) spacer, and n is from 1 to 200. Within other embodiments, the oligonucleotide is covalently bound by a heterobifunctional linker, such as succinimidyl 4-(N-maleimidomethyl) cyclohexane-1-carboxylate).

These and other aspects of the present invention will become evident upon reference to the following detailed description and attached drawings. In addition, various references are set forth below which describe in more detail certain procedures or compositions (e.g., plasmids, etc.), and are therefore incorporated by reference in their entirety.

BRIEF DESCRIPTION OF THE DRAWINGS

FIG. 9 is a table which summarizes the data shown in FIGS. 7 and 8.

DETAILED DESCRIPTION OF THE INVENTION

Figure 1:
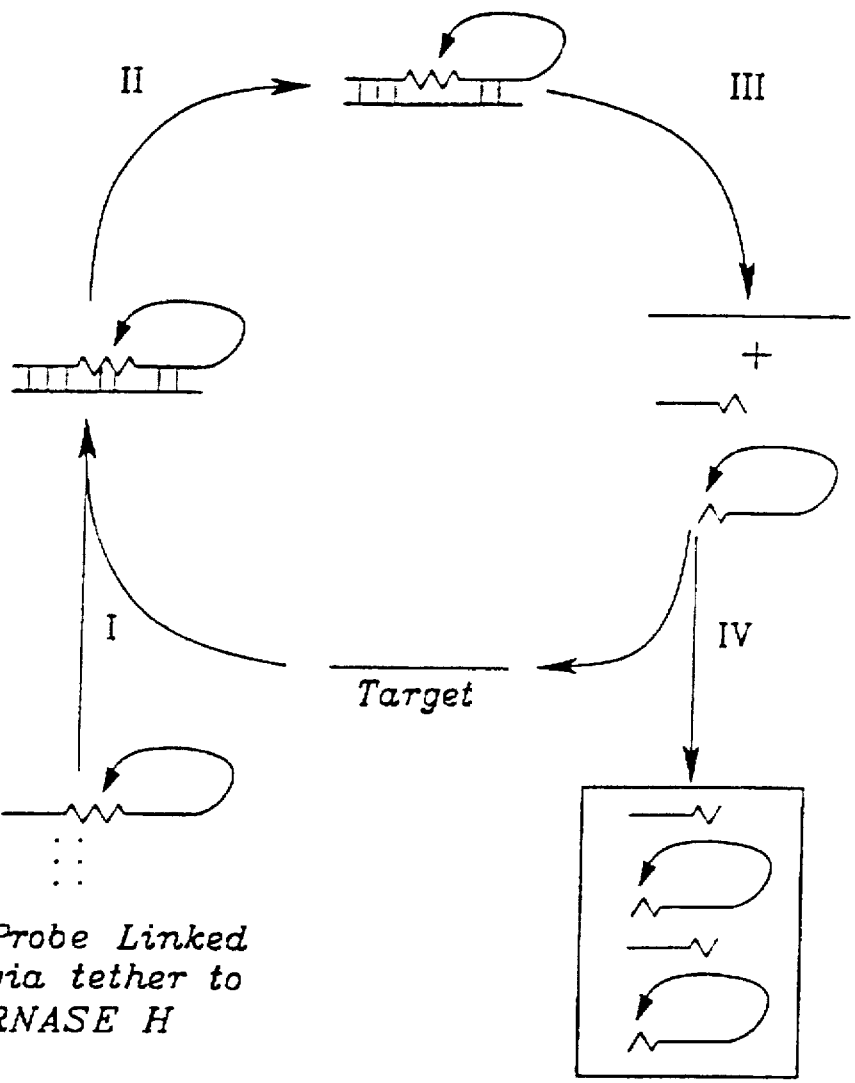
FIG. 1 is a schematic illustration of a cycling probe reaction utilizing a probe covalently linked to RNase H.
Figure 2:
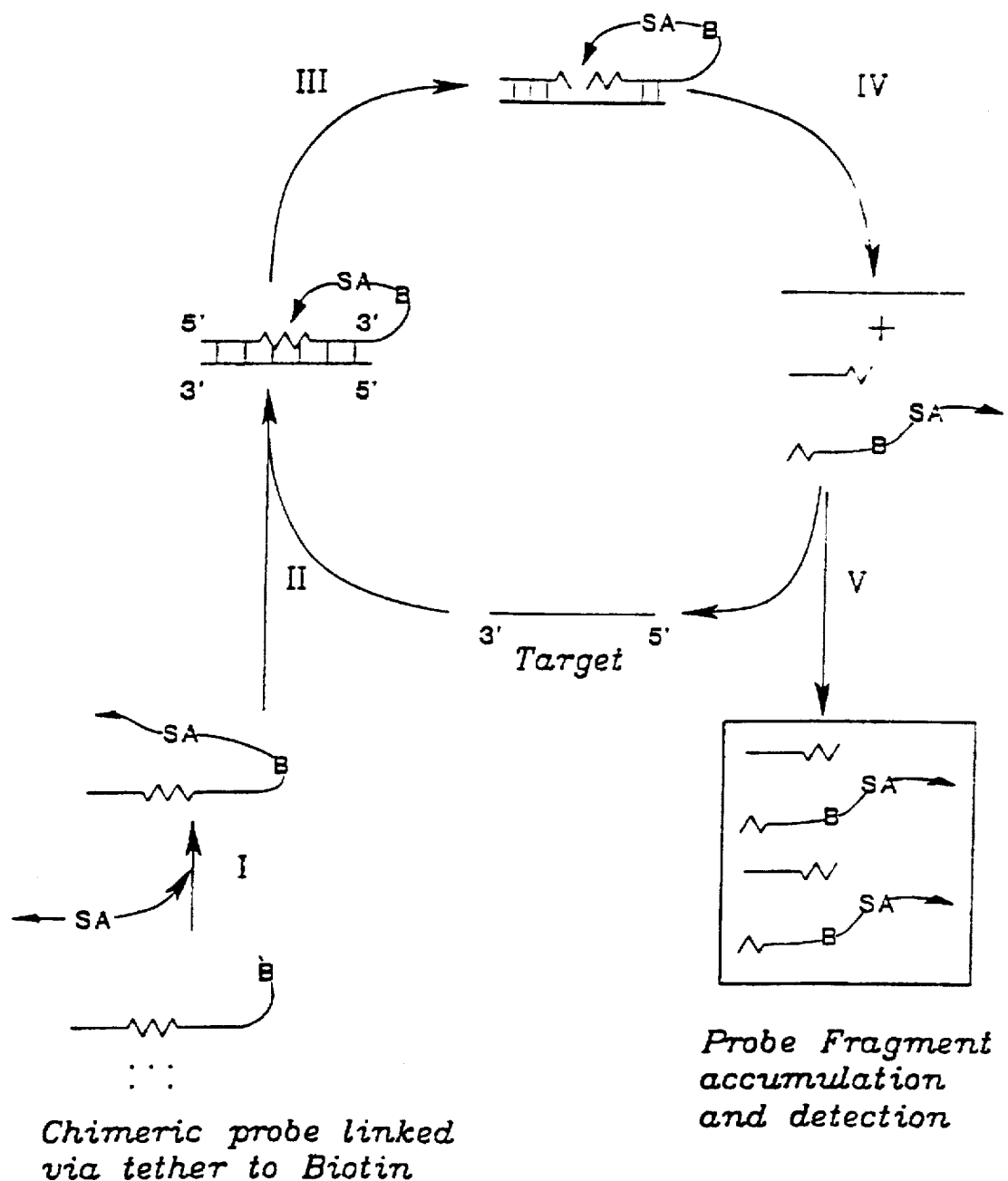
FIG. 2 is a schematic illustration of a cycling probe reaction utilizing a probe linked to RNase H through a biotin-streptavidin linkage.
Figure 3:
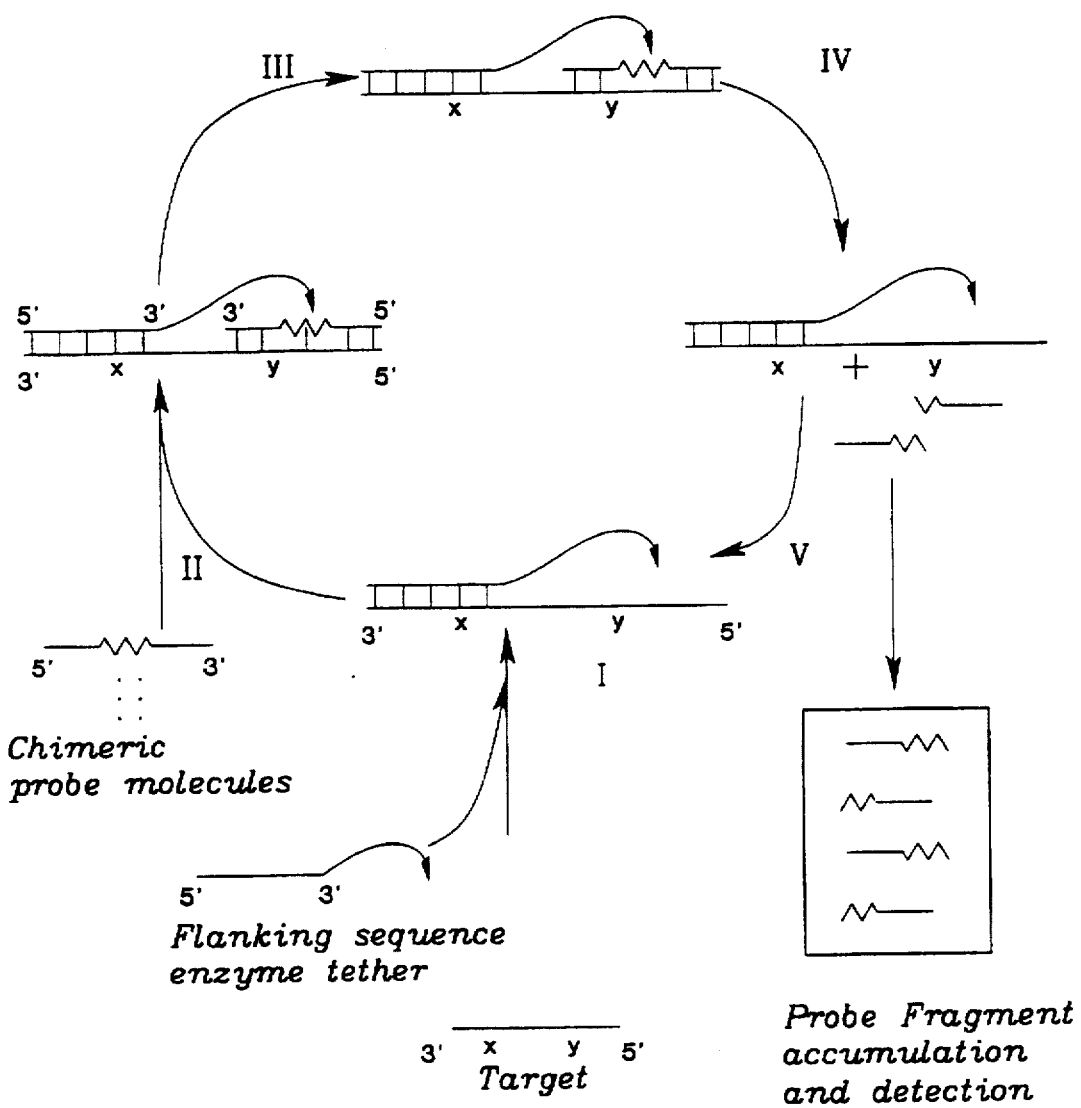
FIG. 3 is a schematic illustration of a cycling probe reaction utilizing an adjacent or flanking sequence covalently linked to an enzyme.
Figure 4:
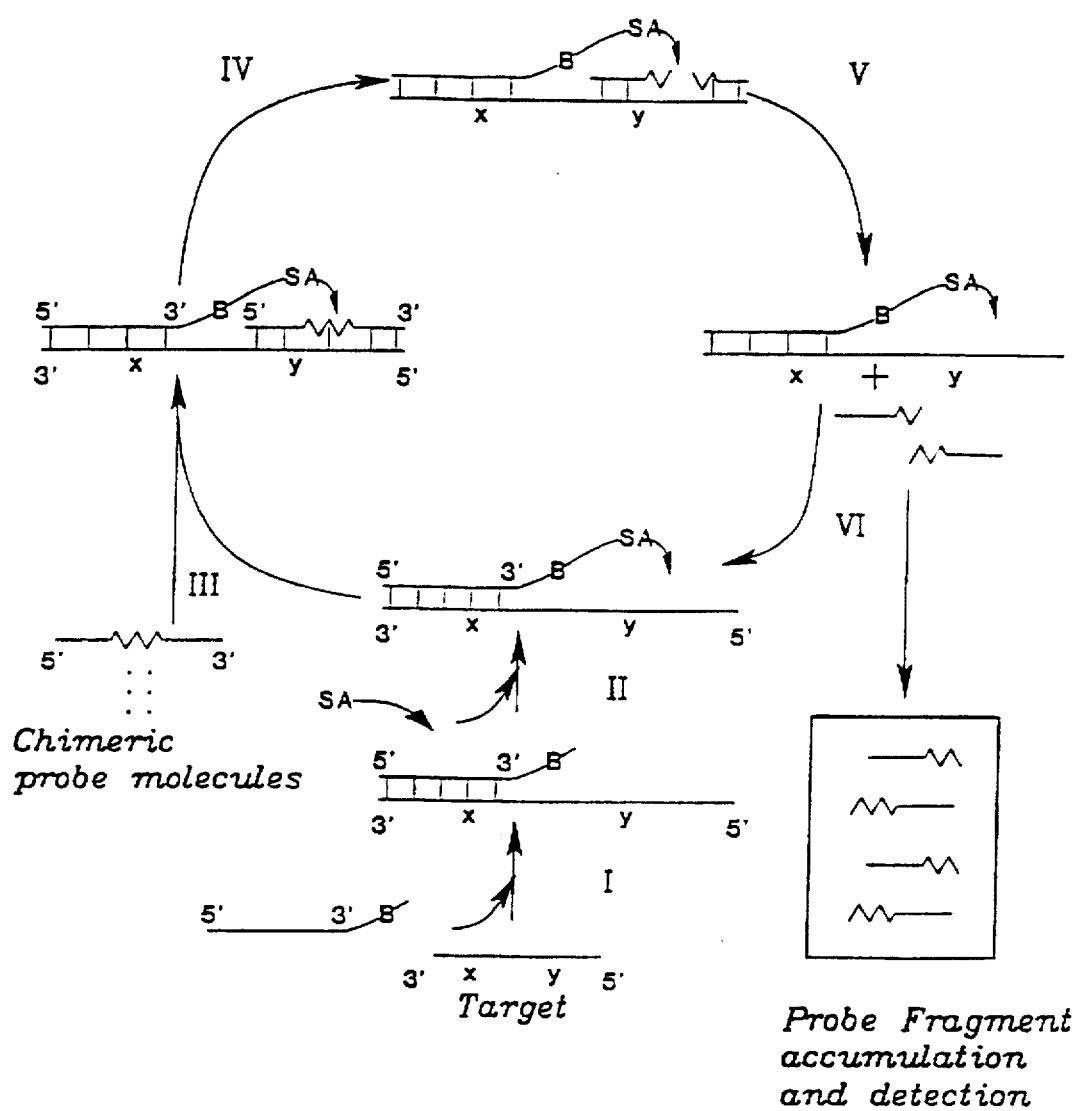
FIG. 4 is a schematic illustration of a cycling probe reaction utilizing an adjacent or flanking sequence linked to RNase H through a biotin-streptavidin linkage.

As noted above, the present invention provides methods for detecting a target nucleic acid comprising the steps of (a) reacting a target nucleic acid molecule, a complementary single-stranded nucleic acid probe having a scissile linkage, and a first complementary adjacent sequence-enzyme molecule under conditions which allow the probe and adjacent sequence-enzyme molecule to hybridize to the target nucleic acid and form a double-stranded, target-probe adjacent sequence complex, wherein the adjacent sequence-enzyme molecule is capable of cleaving the probe at the scissile linkage, such that one or more portions of the nucleic acid probe are released from the target-probe adjacent sequence complex, and (b) detecting the released portions of the nucleic acid probe, and thereby determining the presence of the target nucleic acid. Within other aspects of the present invention, methods are provided for detecting a target nucleic acid comprising the steps of (a) reacting a target nucleic acid molecule and a complementary single-stranded nucleic acid probe having a scissile linkage and an attached enzyme molecule under conditions which allow the target nucleic acid and probe to hybridize to each other and form a double-stranded, target-probe complex, wherein the enzyme molecule is capable of cleaving the probe of the target-probe-adjacent sequence complex of the target-probe complex at the scissile linkage, such that one or more portions of the nucleic acid probe are released from the target-probe-adjacent sequence complex, and (b) detecting the released portions of the nucleic acid probe, and thereby determining the presence of the target nucleic acid.

Such methods may be utilized to detect any of a variety of target nucleic acid molecules. Representative examples of target nucleic acid molecules include nucleic acid molecules obtained from mammalian cells (e.g., human, macaque, horse, cow, sheep, pig, dog, cat, rat or mouse cells), fungal cells, bacterial cells, plants, viruses and bacteriophage. Methods for selecting target nucleic acid molecules, as well as methods for generating target nucleic acid molecules may be readily accomplished by one of ordinary skill in the art given the disclosure provided herein (see generally, Sambrook et al., *Molecular Cloning: A Laboratory Manual* (2d ed.), Cold Spring Harbor Laboratory Press, 1989).

As noted above, within one aspect of the present invention the target nucleic acid molecule is reacted with a complementary single-stranded nucleic acid probe having a scissile linkage. Briefly, A wide variety of nucleic acid probes having scissile linkages may be utilized within the context of the present invention. Preferably, the probe is designed such that, upon cleavage by an enzyme which is capable of specifically cleaving the probe-target complex at the scissile link, probe portions are released which are detectable (see U.S. Pat. Nos. 4,876,187, 5,011,769 and 5,403,711). Preferred probe molecules of the present invention generally have the structure $[(NA_1)_x (—S—)_z (—NA_2)_y]_n$ wherein $NA_1$ and $NA_2$ are molecules composed of nucleic acids or nucleic acid analogues, —S— is a scissile linkage and x, y, and z are integers from 1–100 and n is an integer from 1–10. Within certain particularly preferred embodiments of the invention, $NA_1$ and $NA_2$ may range from 3 to 40 nucleotides, and when S is composed of nucleic acids, may range in size from 2 to 20 nucleotides. In addition, it should be understood that as utilized within the context of the present invention, each of x, y and z can vary with each iteration of n. Although within various embodiments of the invention a single-stranded probe is utilized to react or hybridize to a single-stranded target sequence, the above-described methods should not be limited to only situations wherein complementary probe and target sequences pair to form a duplex.

Within one embodiment, $NA_1$ and $NA_2$ as described above are DNA molecules which may or may not have the same sequence. Alternatively, $NA_1$ and $NA_2$ may be constructed of RNA molecules, which may or may not have the same sequence, or a combination of RNA and DNA molecules. The DNA or RNA molecules utilized may be derived from naturally occurring sources, or they may be synthetically formed. Each of $NA_1$ and $NA_2$ may be from about 5 bases to 10,000 bases in length.

Within other embodiments, $NA_1$ or $NA_2$ may be composed of nucleic acid analogues such as methyl phosphonates, carbamates, amidates, triesters, or "Peptide Nucleic Acids" ("PNA"). For example, PNA oligomers can hybridize to complementary target oligonucleotides (DNA or RNA) sequences with very high specificity. Such duplexes are more stable than the corresponding DNA-DNA or DNA-RNA duplexes (Egholm et al., *Nature* 365:556–568, 1993). Furthermore, PNA can bind to double stranded (ds) DNA by strand displacement (Nielsen et al., *Science* 254:1497–1500, 1991) and hence may obviate the traditional double strand denaturation requirement in sample preparation. Low concentration salt is generally preferred for binding of PNA to dsDNA ($\leq 50$ mM/L of $Na^+$). Moderate concentration of salt can inhibit binding through double strand displacement of PNA to dsDNA. However, once bound the PNA/DNA duplexes are stable to high concentration of salt. Further, these duplexes are also thermally stable compared to oligonucleotide/oligonucleotide duplexes (duplexes of PNA/DNA are more stable by approximately 1° C. per base pair compared to corresponding DNA/DNA). Based on the requirement of high sequence specificity to the target oligonucleotide, greater thermal stability and resistance to high salt concentration of the duplex once formed, PNAs are often ideal molecules for use in the methods described herein. Within certain embodiments, two short PNAs may be linked with scissile linkage and used as a highly sequence specific probe.

Probes of the present invention may also have one or more detectable markers attached to one or both ends (e.g., $NA_1$ or $NA_2$). The marker may be virtually any molecule or reagent which is capable of being detected, representative examples of which include radioisotopes or radiolabeled molecules, fluorescent molecules, fluorescent antibodies, enzymes, or chemiluminescent catalysts.

As noted above, the nucleic acid probe has a scissile linkage which is capable of being cleaved or disrupted without cleaving or disrupting any nucleic acid sequence of the molecule itself, or of the target nucleic acid sequence. As used within the context of the present invention, a scissile linkage is any connecting chemical structure which joins two nucleic acid sequences, and which is capable of being selectively cleaved without cleavage of the nucleic acid sequences to which it is joined. The scissile linkage may be a single bond or a multiple unit sequence. An example of such a chemical structure is an RNA molecule. Other chemical structures which may be suitable as a scissile linkage are DNA molecules, an amino acid sequence, an abasic nucleotide molecule or any carbohydrate polymer (e.g., cellulose or starch). When the scissile linkage is a nucleic acid molecule, it should differ from the nucleic acid sequence of $NA_1$ and $NA_2$.

In the nucleic acid probes described above, when n is greater than one, the unit $NA_1$—S—$NA_2$ repeats. As should be readily understood by one of ordinary skill in the art given the disclosure provided herein, the unit may be the same within each repeat, or may vary randomly in a defined pattern. In addition, the scissile linkage may also vary from unit to unit. For example, one scissile linkage may be an amino acid sequence, and another an RNA molecule.

As noted above, the probes of the present invention may also be linked to a solid support either directly, or through a chemical linker. Representative examples of solid supports include silicaceous, cellulosic, polymer-based, or plastic materials.

Within a particularly preferred embodiment of the invention, nucleic acid probes have the structure: $[NA_1$—

S—NA$_2$]$_n$ wherein NA$_1$ and NA$_2$ are nucleic acid sequences, S is a scissile nucleic acid linkage, and n is an integer from 1 to 10. Within this embodiment, NA$_1$ and NA$_2$ are different nucleic acid sequences which are noncomplementary to each other, and —S— is a scissile linkage which is capable of being cleaved or disrupted without cleaving or disrupting NA$_1$ or NA$_2$, or a target nucleic acid sequence capable of hybridizing to the NA$_1$ or NA$_2$ sequences, wherein if the scissile linkage is a nucleic acid sequence it is RNA when both NA$_1$ and NA$_2$ are DNA sequences, or the scissile linkage is DNA when both NA$_1$ and NA$_2$ are RNA sequences.

Methods for constructing such nucleic acid probes (and adjacent or flanking sequence oligonucleotides, as described below), may be readily accomplished by one of ordinary skill in the art, given the disclosure provided herein. Particularly preferred methods are described for example by: Matteucci and Caruthers, *J. Am. Chem. Soc.* 103:3185,1981; Beaucage and Caruthers, *Tetrahedron Lett.* 22:1859–1862, 1981; U.S. Pat. Nos. 4,876,187 and 5,011,769; Ogilvie et al., *Proc. Natl. Acad. Sci. USA* 85:8783–8798, 1987; Usman et al., *J. Am. Chem. Soc.* 109:7845–7854, 1987; Wu et al., *Tetrahedron Lett.* 29:4249–4252, 1988; Chaix et al., *Nuc. Acids Res.* 17:7381–7393, 1989; Wu et al., *Nuc. Acids Res.* 17:3501–3517, 1989; McBride and Caruthers, *Tetrahedron Lett.* 24:245–248, 1983; Sinha et al., *Tetrahedron Lett.* 24:5843–5846, 1983; Sinha et al., *Nuc. Acids Res.* 12:4539–4557, 1984; and Gasparutto et al., *Nuc. Acids Res.* 20:5159–5166, 1992.

Preferably, nucleic acid probes and adjacent sequence molecules may be synthesized utilizing standard chemistries on automated, solid-phase synthesizers such as Applied Biosystems, Inc.'s Model 391 DNA Synthesizer (PCR-MATE EP) or Applied Biosystems, Inc.'s Model 394 DNA/RNA Synthesizer. Briefly, oligonucleotide synthesis is accomplished in cycles wherein each cycle extends the oligonucleotide by one nucleotide. Each cycle consists of four steps: (1) deprotecting the 5'-terminus of the nucleoside or oligonucleotide on the solid support, (2) coupling the next nucleoside phosphoramidite to the solid phase immobilized nucleotide, (3) capping the small percentage of the 5'-OH groups of the immobilized nucleotides which did not couple to the added phosphoramidite, and (4) oxidizing the oligonucleotide linkage to a phosphotriester linkage.

Within one embodiment of the invention, oligonucleotides may be synthesized essentially as described below. Briefly, a solid phase is selected on which the first nucleoside is attached to the support by a base labile succinate linkage. The selection of the appropriate solid phase will depend upon the base at the sequence's 3'-terminus. The nucleoside attached to the 3'-terminus is deblocked to make to make available the 5'-OH for condensation with the next phosphoramidite. The dimethoxytrityl group which protects the 5'-OH of the immobilized nucleoside is removed by treatment with a di- or trichloroacetic acid solution. The next phosphoramidite is then added along with an activator, tetrazole, to couple the 5'-OH of the immobilized nucleotide to the added phosphoramidite forming a phosphite triester linkage. Any remaining uncoupled 5'-OH groups are then capped by the addition of an acetic anhydride solution, catalyzed by N methyl imidazole. The capping of uncoupled 5'-OH groups ensures that only oligonucleotides of defined sequence will undergo further chain lengthening. The last step in the synthesis cycle is the oxidation of the phosphite triester linkage to the more stable phosphate triester linkage. The oxidation is accomplished by the addition of an aqueous iodine solution. The four steps of this synthesis cycle are then repeated until the desired oligonucleotide sequence has been prepared.

Reagents for the synthesis of probes as described above are commercially available from a variety of sources, including Applied Biosystems Inc. (Foster City, Calif.), Glen Research (Sterling, Va.), Biogenex, and Millipore Corp. (Bedford, Mass.). For DNA synthesis, preferred phosphoramidites have base-labile protecting groups. Representative examples may be readily obtained from Applied Biosystems, Glen Research and Millipore Corp. Similarly, for RNA synthesis, preferred phosphoramidites are the base labile ones available from Glen Research and Millipore Corp.

The result of the above synthesis is a N-base protected oligonucleotide phosphotriester immobilized on a solid support. In the case of RNA synthesis, in addition to the N-base protecting groups, the immobilized phosphotriester also is 2'-OH protected. In order to prepare the desired oligonucleotide, the modified form of the oligonucleotide should be cleaved from the solid support, the phosphotriester converted to the phosphodiester linkage native to DNA and RNA, and the bases N-deprotected. In addition, in the case of RNA synthesis, the 2'-OH group should also be deprotected.

Treatment of the solid support bearing the modified oligonucleotide with aqueous ammonia releases the 3'-OH group and cleaves the oligonucleotide from the solid support. The ammonia treatment also removes the cyanoethyl group of the phosphate triester to produce the desired phosphodiester. Within one embodiment of the invention, for a 0.2 umole synthesis, the solid phase is treated successively with three portions of 0.8 ml each 28%–30% aqueous ammonium hydroxide. The solid support is treated with each portion for 15 minutes at room temperature, and then the solutions are combined. The resulting ammonia solution contains an oligonucleotide in which its bases are N-protected, and in the case of RNA synthesis, the 2'-OH group also remains protected.

The labile N-base protecting groups may be removed from the oligonucleotides by allowing the above ammonia solution to stand overnight at room temperature. The ammonia treatment will be effective only when base labile N-protecting groups are present in the original phosphoramidite synthesis reagent. The cyanoethyl phosphoramidites available from Applied Biosystems and Glen Research and Millipore Corp. are preferred for this reason. In the case of DNA synthesis, the overnight treatment with ammonia yields a deoxyoligonucleotide which is ready for purification and use. However, in the case of RNA synthesis, the overnight ammonia treatment yields a deoxyoligonucleotide in which the ribosyl groups remain 2'-OH protected.

The 2'-OH ribosyl protecting group (t-butyldimethylsilyl group) of the synthesized deoxyoligonucleotide is preferably removed after an initial purification of the oligonucleotide by high performance liquid chromatography (HPLC). In a typical purification, the above described ammonia solution containing the 2'-OH protected deoxyoligonucleotide is concentrated to dryness. The RNA residue is dissolved in 100 ml of 10% buffer B (95% acetonitrile in 100 mM triethylammonium acetate) and 90% buffer A (5% acetonitrile in 100 mM triethylammonium acetate). The resulting solution is centrifuged at 14,000 RPM and the supernatant withdrawn. The solution is then ready for HPLC purification. The oligonucleotide may be purified on a Millipore HPLC Waters 600E Control System using a Millipore Delta Pak (5u C18 300A, 3.9 X 150 mm) Analytical Column eluting with buffers A and B, as described above, operating in a linear gradient mode (10 to 61% B, 10% B for the first 5 minutes then increasing to 61% B by 22 minutes).

The product elutes at approximately 50% B. The fractions containing purified product may then be pooled and transferred to two 2.0 ml tubes to be evaporated to dryness. The resulting HPLC purified 2'-OH protected deoxyoligonucleotide may then be deprotected.

The t-butyldimethylsilyl 2'-OH ribosyl protecting groups may be removed by treatment with a fluoride solution. Briefly, within one embodiment, 0.25 ml of 1.0M tetrabutyl ammonium fluoride in tetrahydrofuran (Aldrich Chemical Co., Milwaukee, Wis.) is first added to each of two tubes. The solutions are allowed to stand overnight at room temperature after which 1.75 to 2.0 ml water is added to each tube. The fully deprotected synthetic RNA may be isolated by size exclusion chromatography. More specifically, for the above preparation four NAP 10 Sephadex G-25 columns (Pharmacia Corp., Piscataway, N.J.) are prepared according to the manufacturer's instructions. One milliliter of the above RNA containing solution is applied to each column. Each column is then eluted with 1.5 ml distilled water, and the eluant collected, combined, and evaporated to dryness. The resulting solid is dissolved in 100 ml buffer A (described above) and centrifuged at 14,000 RPM for 5 minutes. The supernatant solution containing the size exclusion purified RNA containing solution is collected and HPLC purified as described above, except that the linear gradient is 0 to 15% B (15% B at 30 minutes). The fully deprotected RNA containing product elutes at about 11% B. The product fractions are then collected, pooled, and evaporated. The yield of the fully deprotected RNA containing product may be quantitated by measuring the absorbance at 260 nm.

Figure 5:
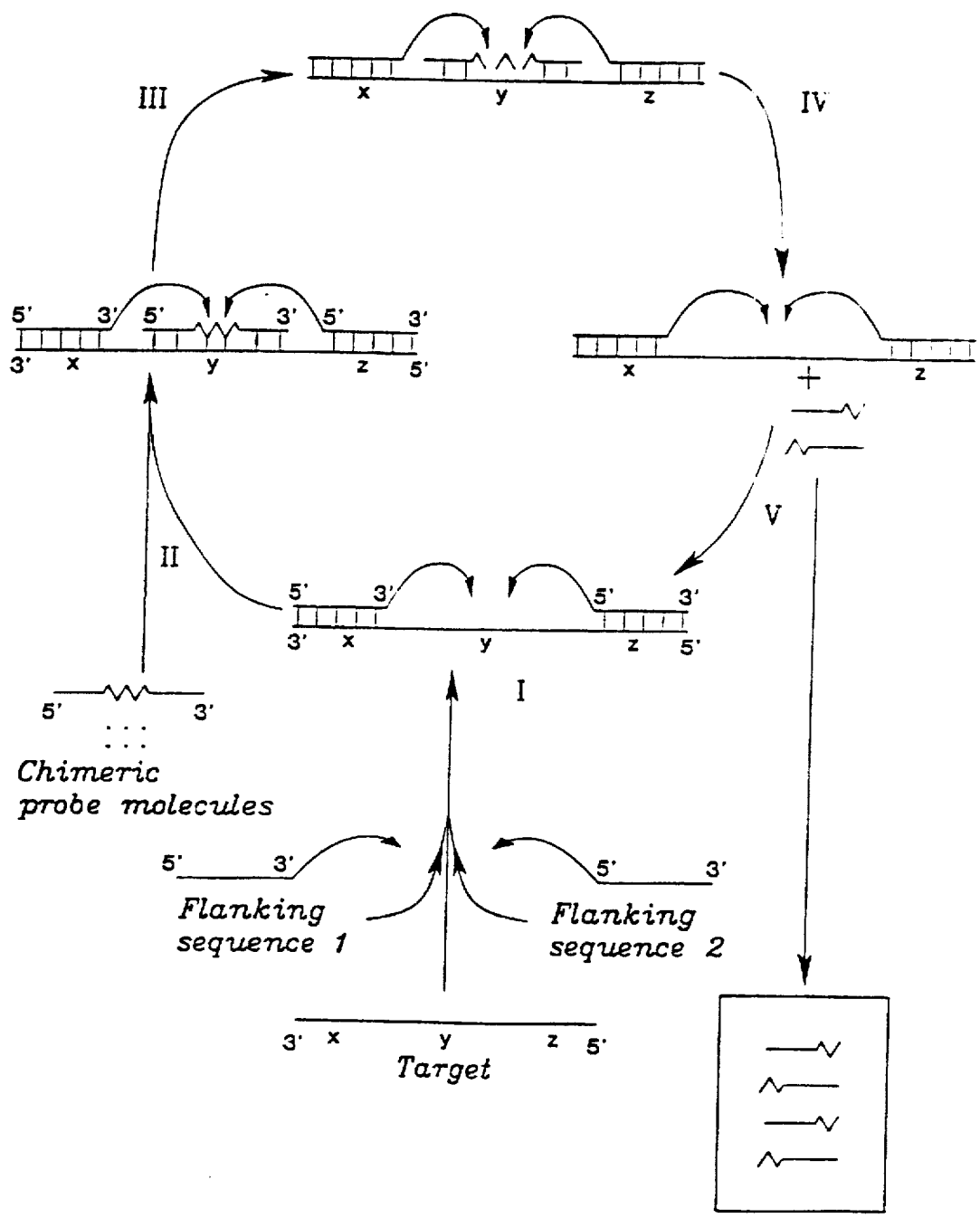
FIG. 5 is a schematic illustration of a cycling probe reaction utilizing two adjacent or flanking sequences, each of which have been linked to RNase H.

As noted above, the present invention also provides adjacent-sequence molecules which may be attached to an enzyme of interest, and utilized in order to increase the efficiency of the detection methods described herein. Briefly, "adjacent sequence-enzyme molecules" refers to a nucleic acid sequence (e.g., composed of nucleic acids or nucleic acid analogues, as described above, or any combination of these) which is linked to an enzyme molecule, and which has been designed to hybridize adjacent to either side of the site to which the single-stranded nucleic acid probe (e.g., within 1, 5, 10, 20 or 50 nucleotides) attaches, such that a cycling reaction may be efficiently completed. When more than one adjacent sequence-enzyme molecule is utilized within the methods described herein (see for example, FIG. 5), the second adjacent sequence-enzyme molecule is preferably selected such that it is complementary to the target nucleic acid molecule and is positioned at an opposing end of the probe as compared to the first adjacent sequence. Methods described above for construction of the nucleic acid probe may likewise be utilized for construction of the adjacent sequence molecule.

CONSTRUCTION OF OLIGONUCLEOTIDE-ENZYME MOLECULES

As noted above, the present invention also provides oligonucleotide-enzyme molecules (e.g., probe-enzyme or adjacent sequence-enzyme molecules), comprising an enzyme capable of cleaving scissile linkages, and a single stranded nucleic acid sequence composed of nucleic acids or nucleic acid analogues (e.g., DNA, RNA or PNA). Such molecules may be constructed by a variety of methods including for example, covalent and non-covalent coupling. For example, within one embodiment of the invention, oligonucleotides may be modified at either the 5'- or the 3'-terminus with a suitable reactive functional group. Alternatively, a reactive functional group may be incorporated into interior positions of the oligonucleotide. Suitable reactive functional groups for use within the present invention include nucleophilic groups such as primary amino and thiol groups. These groups may be readily incorporated into the oligonucleotide during the automated synthesis of the oligonucleotide. For example, using "AminoLink 2" (Applied Biosystems Inc., Foster City, Calif., part no. 400803, ABI User Bulletin No. 49) as a reagent in the automated synthesis of the oligonucleotide (PCR-MATE EP Model 391 DNA Synthesizer, ABI, Foster City, Calif.), a primary amino group may be covalently attached during the final coupling cycle to the 5'-terminus of the synthetic oligonucleotide. Cleavage from the solid support and purification by high pressure liquid chromatography provides an amino-modified synthetic oligonucleotide suitable for coupling to a variety of other molecules such as those mentioned above. Utilizing similar reagents and methodologies, 3'-amino, as well as, 5'- and 3'-thiol modified oligonucleotides may be prepared.

To effect the covalent coupling of the amino-modified oligonucleotide to another molecule, the other molecule should be suitably reactive, that is, capable of forming a covalent bond with the reactive functional group on the oligonucleotide. Typically for amino-modified oligonucleotides, their coupling partners bear reactive carboxylic acid derivatives which result in the formation of an amide link between the oligonucleotide and the other molecule. Many varieties of reactive carboxylic acid derivatives are suitable for coupling. Suitable reactive groups include activated esters such as n-hydroxysuccinimide derivatives, mixed anhydrides, and acid halides among others. Preferred carboxylic reactive groups include N-hydroxysuccinimide esters. For example, carboxylic derivatives of biotin and fluorescein, a widely used fluorescent dye, are commercially available from many sources and are routinely used to label amino-modified oligonucleotides as well as other biological molecules which bear reactive amino groups. Biotin and fluorescein amidites, N-hydroxysuccinimide esters of biotin and fluorescein are commercially available.

In the present invention, a suitable linker may be covalently attached to the amino-modified oligonucleotide to facilitate attachment to and function of the enzyme of interest (e.g., RNase H). The linker should be flexible and sufficiently long to allow the active site of the enzyme to reach and act upon the substrate, the scissile portion of the oligonucleotide probe. Additionally, the linker should be bifunctional with regard to its reactivity such that the linker may form a covalent bond with the oligonucleotide and the enzyme. Suitable linkers include for example heterobifunctional agents which are designed for protein coupling and modifications. (See, e.g., Means and Feeney, *Chemical Modification of Proteins*, Holden-Day, 1971.) As utilized herein, the term "heterobifunctional" refers to the fact that the agent bears two reactive functional groups as coupling sites which are different from each other and therefore capable of selective coupling to two different binding partners, for instance, an amino-modified oligonucleotide and a thiol-modified enzyme. Suitable tethers include commercially available heterobifunctional coupling agents such as succinimidyl 4-(N-maleimidomethyl)cyclohexane-1-carboxylate, "SMCC," (Pierce Chemical Co., Rockford, Ill., part no. 22320 H). Briefly, SMCC bears an N-hydroxysuccinimide group which when reacted with an amine such as an amino-modified oligonucleotide forms an amide linkage between the oligonucleotide and the tether. SMCC also bears an N-methylmaleimide group which is selectively reactive toward thiol groups. The length and flexibility of the SMCC linker is defined by the cyclohexane segment which joins the two reactive groups. One skilled in the art may vary the segment which joins these reactive groups to achieve the flexibility and length necessary for the function of the probe of the present invention. Accordingly, reaction of the amino-modified oligonucleotide with SMCC produces an tethered oligonucleotide which, by virtue of the N-methyl maleimide group, is capable of further tethering to a second molecule suitably functionalized with a thiol group.

Once the tethered oligonucleotide bearing the N-methylmaleimide functional group is synthesized, reaction with any thiol bearing molecule will result in the covalent attachment of the linked oligonucleotide to the thiol bearing molecule through the formation of a carbon-sulfur covalent bond. In the present invention, the thiol bearing molecule is the enzyme of interest, which bears a single reactive thiol group, a cysteine residue. Alternatively, for those molecules which do not contain thiol groups, thiol groups may be incorporated into these molecules by standard chemical methods. (See, e.g., Means and Feeney, supra) Therefore, reaction of the linked oligonucleotide with the enzyme of interest results in covalent bond formation between the enzyme thiol and the tether maleimide, and provides the tethered enzyme—nucleic acid probe of the present invention. The probe thus produced is a 1:1 complex of enzyme to oligonucleotide in which the enzyme and oligonucleotide are spatially separated by the tether.

A wide variety of enzymes may be linked given the disclosure provided herein, including for example RNases such as RNase H derived from eukaryotic or prokaryotic organisms. Within one embodiment, thermophilic enzymes such as thermophilic RNase H are particularly preferred.

Biotin - Streptavidin linkages

Within a further embodiment of the invention, the nucleic acid probe (or flanking or adjacent sequence oligonucleotide) may be biotinylated, in order to facilitate binding to an avidinated or streptavidinated enzyme. Within a preferred embodiment of the invention, the nucleic acid probe is bound to RNase H through a streptavidin-biotin linkage.

Briefly, biotinylated oligonucleotides may be prepared by the covalent coupling of a reactive form of biotin (typically, an N-hydroxysuccinimide ester) with a suitably reactive oligonucleotide (typically, a 5'-amino modified oligonucleotide prepared by coupling a suitable amino containing phosphoramidite, i.e., AminoLink from Applied Biosystems Inc., in the last step of an automated, solid-phase oligonucleotide synthesis). Alternatively, the biotinylated probe may be prepared directly by using a biotin phosphoramidite during the automated, solid-phase synthesis of the oligonucleotide probe.

Suitable biotin phosphoramidite reagents are commercially available. For example, biotin phosphoramidite and biotin-dT (also a phosphoramidite), are available from Glen Research and are specifically designed for automated oligonucleotide synthesis. The former reagent is useful for incorporating a functional biotin at either the 3'- or 5'-terminus of an oligonucleotide, while the latter may be used to incorporate biotin into the oligonucleotide at any position within the oligonucleotide.

Streptavidin-enzyme molecules may also readily be constructed given the disclosure provided herein. A particularly preferred streptavidin-RNase H fusion molecule is set forth in more detail below in Example 2.

Cycling-Probe Reactions

As noted above, cycling reactions for the detection of a desired target nucleic acid molecule may be readily performed according to the general steps of (a) reacting a target nucleic acid molecule, a complementary single-stranded nucleic acid probe having a scissile linkage, and a first complementary adjacent sequence-enzyme molecule under conditions which allow the probe and adjacent sequence-enzyme molecule to hybridize to the target nucleic acid and form a double-stranded, target-probe adjacent sequence complex, wherein the adjacent sequence-enzyme molecule is capable of cleaving the probe at the scissile linkage, such that one or more portions of the nucleic acid probe are released from the target-probe adjacent sequence complex, and (b) detecting the released portions of the nucleic acid probe, and thereby determining the presence of the target nucleic acid.

Other cycling reactions which may be performed include reacting a target nucleic acid molecule, a complementary single-stranded nucleic acid probe having a scissile linkage, and a first complementary adjacent sequence-enzyme molecule under conditions which allow the probe and adjacent sequence-enzyme molecule to hybridize to the target nucleic acid and form a double-stranded, target-probe-adjacent sequence complex. Particularly preferred embodiments of the cycling probe reaction are described in more detail below in Example 5. In addition, schematic illustrations of various reactions have been provided as noted above in FIGS. 1–5.

The following examples are offered by way of illustration, and not by way of limitation.

EXAMPLES

Example 1

CONSTRUCTION OF OLIGONUCLEOTIDE PROBES

Probe molecules are constructed as generally described by Matteucci and Caruthers, *J. Am. Chem. Soc.* 103:3185, 1981; Beaucage and Caruthers, *Tetrahedron Lett.* 22:1859, 1981; see also U.S. Pat. Nos. 4,876,187 and 5,011,769. In particular, oligonucleotides are synthesized on an Applied Biosystems, Inc. Model 391 DNA Synthesizer (PCR-MATE-EP™) utilizing protocols described by the manufacturer, and CE-phosphoramidite reagents from Glen Research (Sterling, Va.).

Utilizing this procedure, the following oligomers are synthesized (capital letters have been utilized to denote deoxyribonucleotides, and lower case letters have been utilized to denote ribonucleotides):

Probe Sequence, (SEQ. ID. NO.: 1)
5'-CAT CAC Cgg aaT TGA AGC C-3'
Probe Target Sequence (SEQ. ID. NO.: 2)
5'-GGC TTC AAT TCC GGT GAT G-3'
Distal Fling Sequence Probe (SEQ. ID. NO.: 3)
5'-TTG CTC GGT GAT GCC CAG CGC CGA ATT C-3'
Distal Flanking Sequence Target, (SEQ. ID. NO.: 4)
5'-GAA TTC GGC GCT GGG CAT CAC CGA GCA A-3'
Proximal Flanking Sequence Probe (SEQ. ID. NO.: 5)
5'-CGT CGG GCG CAG CCC ACG GGA CGC GGC AGG-3'
Proximal Fling Sequence Target (SEQ. ID. NO.: 6)
5'-CCT GCC GCG TCC CGT GGG CTG CGC CCG ACG-3'

Example 2

CONSTRUCTION OF STREPTAVIDIN - RNASE H

A. Construction of Streptavidin-RNase H fusion protein

1. Construction of pIDB1

Genomic DNA from *T. thermophilus* (ATCC No. 27634) is amplified by PCR utilizing primers BC202 and BC203 (Table 1 below), and cloned as blunt end fragment(s) into the Sma I site of pTZ19R (Pharmacia, Piscataway, N.J.). The resultant plasmid is designated pIDB1.

2. Construction of pIDB2

A fragment from pIDB1 is amplified utilizing primers BC214 and BC202 (see Table 1 below), and cloned into the Sma I site of pTZ19R as a blunt end fragment. This plasmid is designated pIDB2b. The EcoRI fragment of pIDB2b is cloned into pT7-7 (Dr. Stan Tabor, Harvard Medical School, Boston, Mass.). The resultant plasmid is designated pIDB2.

3. Construction of pIDB9

In order to obtain the RNase H gene expressed in its native form, primers FB102 and BC202 (see Table 1 below) were utilized to amplify the corresponding fragment from pIDB1, and clone it as a blunt end fragment into the Sma I site of pTZ19R. The resultant plasmid is designated pIDB6. The restriction fragment Nde I - EcoRI from pIDB6 is then cloned into pT7-7 (available from U.S. Biochemical, Cleveland, Ohio, catalogue No. 71883; see also Tabor and Richardson, *PNAS* 262:1074–1078, 1985) to generate pIDB9. This plasmid contains the RNase gene expressed in its native form.

4. Construction of pIDB10: a Streptavidin-RNase H fusion protein

The sequence encoding RNase H is first PCR amplified from pIDB1 utilizing primers FB102 and BC202 (Table 1). The amplified fragment is kinased and ligated into the vector pTSA-18F that has been previously cut with SmaI and treated with phosphatase. The vector pTSA-18F (Sano and Cantor, *B.B.R.C.* 176:571–577, 1991; U.S. Pat. No. 4,839,293), contains a DNA fragment coding for a truncated form of streptavidin, which is controlled by the T7 promoter. The resultant plasmid is designated pIDB10.

pIDB10 expresses a streptavidin-RNase H fusion protein which is 293 amino acids in length. In particular, pIDB10 encodes amino acid residues 16 to 133 of the mature streptavidin at the N-terminus in-frame with amino acids 1 to 166 of T. th. RNase H. The streptavidin-RNase H junction of pIDB10 is confirmed by determining the DNA sequence.

5. Construction of pIDB11: a Streptavidin-RNase H fusion protein

The sequence encoding RNase H is first PCR amplified from pIDB2 utilizing primers FB106 and FB107, cut with EcoRI and HindIII and cloned into the same sites in pTSA-18F. This plasmid is designated pIDB11. This plasmid expresses a streptavidin-RNase H fusion protein which is 287 amino acids in length.

TABLE 1

| Designation | SEQ. ID. No. | Sequence 5' to 3' |
|---|---|---|
| BC202 | 7 | CCG AAT TCT TAT GCC TCT TCG TGA |
| BC203 | 8 | CCG AAT TCA ACC CCT CCC CCA GGA |
| BC214 | 9 | CCG AAT TCC CTC CCC CAG GAA AC |
| FB102 | 10 | CCG CAT ATG AAC CCC TCC CCC AGG |
| FB106 | 11 | AAG GTG AAT TCA ATG AAC CCC TCC CCC AGG |
| FB107 | 12 | ACC AAG CTT CTT ATG CCT CTT CGT GAA |

B. Expression and Purification pIDB10 and pIDB11 are transfected into the bacterial strain NM522 (Gough and Murray, *J. Mol. Biol.* 166:1–19, 1983). Expression of the fusion gene is controlled by the T7 promoter. T7 RNA polymerase is supplied by infecting the transformed strains with an M13 phage containing the T7 polymerase gene under control of the lac UV5 promoter (Studier and Moffatt, *J. Mol. Biol.* 189:113–130, 1986; Studier et al., *Meth. Enzymol.* 185:60–89, 1990).

The streptavidin-RNase H fusion protein is purified from transformed NM522 containing pIDB10 or pIDB11 essentially as described below. Briefly, NM522 cells containing pIDB10 and pIDB11 is grown at 37° C. in 1 L of 2x YT medium (2xYT =10 g yeast extract, 16 g Bacto-tryptone, 5 g NaCl per liter, pH 7.0) containing 0.05 mg/ml ampicillin overnight. When the culture has reached an O.D.$_{600}$ of 0.3, IPTG is added to a final concentration of 0.3 μm in order to induce the lac operon. After 30 min., 15–30 mL of M13 phage (approximately $5 \times 10^9$ pfu/ml) containing the T7 RNA polymerase gene is added to initiate transcription of the fusion gene. The cells are then grown for an additional 3–4 hours before harvest.

Cells are harvested by centrifugation at 2900 xg for 15 min. at 4° C. Cell pellets are resuspended in 30 mL of lysis buffer (1M Tris, pH 7.4, 1 mM EDTA), and stored frozen at −70° C. After thawing, cells are lysed using a French press and centrifuged at 39000x g for 15 min. at 4° C. The pellet is resuspended in Urea buffer (20 mM sodium acetate, pH 5.5, 8M urea), and homogenized using a 20.5 gauge needle and syringe. The sample is again clarified by centrifugation at 39000x g for 15 min. The protein solution is applied to a 2 mL phosphocellulose (Sigma) column connected to an FPLC system (Pharmacia, Piscataway, N.J.), which has been equilibrated with Urea buffer. The column is washed with 8M urea, 0.2M NaCl and the protein is eluted using a 0.2 to 0.7M NaCl linear gradient in 8M urea, 20 mM NaOAc, pH 5.5. Fractions are pooled and dialysed overnight without stirring in 0.2M ammonium acetate, pH 6.0, 0.1 mM EDTA, and 0.02% NaN$_3$.

The fractions are dialysed briefly against loading buffer (1M NaCl, 50 mM sodium carbonate, pH 10.5), then centrifuged at 39,000xg for 15 minutes. The sample is then applied to a 1.2×1.5 2-iminobiotin-agarose column Sigma Chemical Co., St. Louis, Mo., pre-equilibrated with loading buffer. The column is washed with loading buffer, and the protein eluted with 6M urea, 50 mM ammonium acetate pH 4.0, and 0.1 mM EDTA. The eluted protein fractions are pooled, and applied to a PD-10 (Pharmacia, Piscataway, N.J.) desalting column equilibrated with 10 mM sodium acetate pH 5.5, and 150 mM NACl. Protein which elutes from the desalting column is concentrated with a Centricon 10 filter (Amicon). The concentration of protein is determined by spectroscopy utilizing a wavelength of 280 nm and a 0.1% solution of protein. Purity is analyzed by SDS-PAGE.

C. Determination of Streptavidin Binding Activity for Biotin

The activity of streptavidin may be determined by a modified ELISA assay essentially as described below. Briefly, varying amounts (i.e., 5, 50 and 500 ng) of fusion protein in Phosphate Buffered Saline ("PBS"), pH 7.0, is coated in duplicate into each well of a microtiter plate for 2 hours. Unbound protein is washed out with TBST buffer (50 mM Tris-HCl pH 7.9, 150 mM NACl, 0.05% Tween 20), and 50 ng biotin-conjugated alkaline phosphatase (Sigma Chemical Co., St. Louis, Mo.) is added. After 60 minutes, p-nitrophenyl phosphate (1 mg/ml) was added to detect alkaline phosphatase activity.

D. RNase H Assay

The activity of RNase H may be measured using either the acid soluble counts method, or the cycling probe technique (CPT™, Duck et al 1990; Duck et al., Clinical Chem. 404:656, 1994; see Example 5).

The acid soluble counts assay is based on previously published method (Dirksen and Crouch, *J. Biol. Chem.* 256:11569–11573, 1981). Briefly, a reaction mix containing 10 mM Tris, pH 9.0, 10 mM MgCl$_2$, 50 μg BSA and 1–3 μM $^3$H-UTP labeled M13 (Kane, *Biochem* 27:3187–3191, 1988) is added to 1 μl enzyme (0.1–0.02 ng). The reaction proceeds for 5–10 min. then stopped by the addition of 50 µl of 0.5 mg/ml carrier tRNA and 150 µl of 20% TCA and placed on ice for 5–10 min. Samples are then centrifuged at 15,000 g for 5 min. at 4° C. 50 µl of the supernatant is added to 5 ml of liquid scintillation fluid. The acid soluble fraction is calculated according to the formula (counts-background)× 4/(time(min.)×49×10$^6$). 49×10$^6$ dpm corresponds to 1 nmole of substrate.

RNase H activity with M13DNA:RNA substrate

Figure 6:
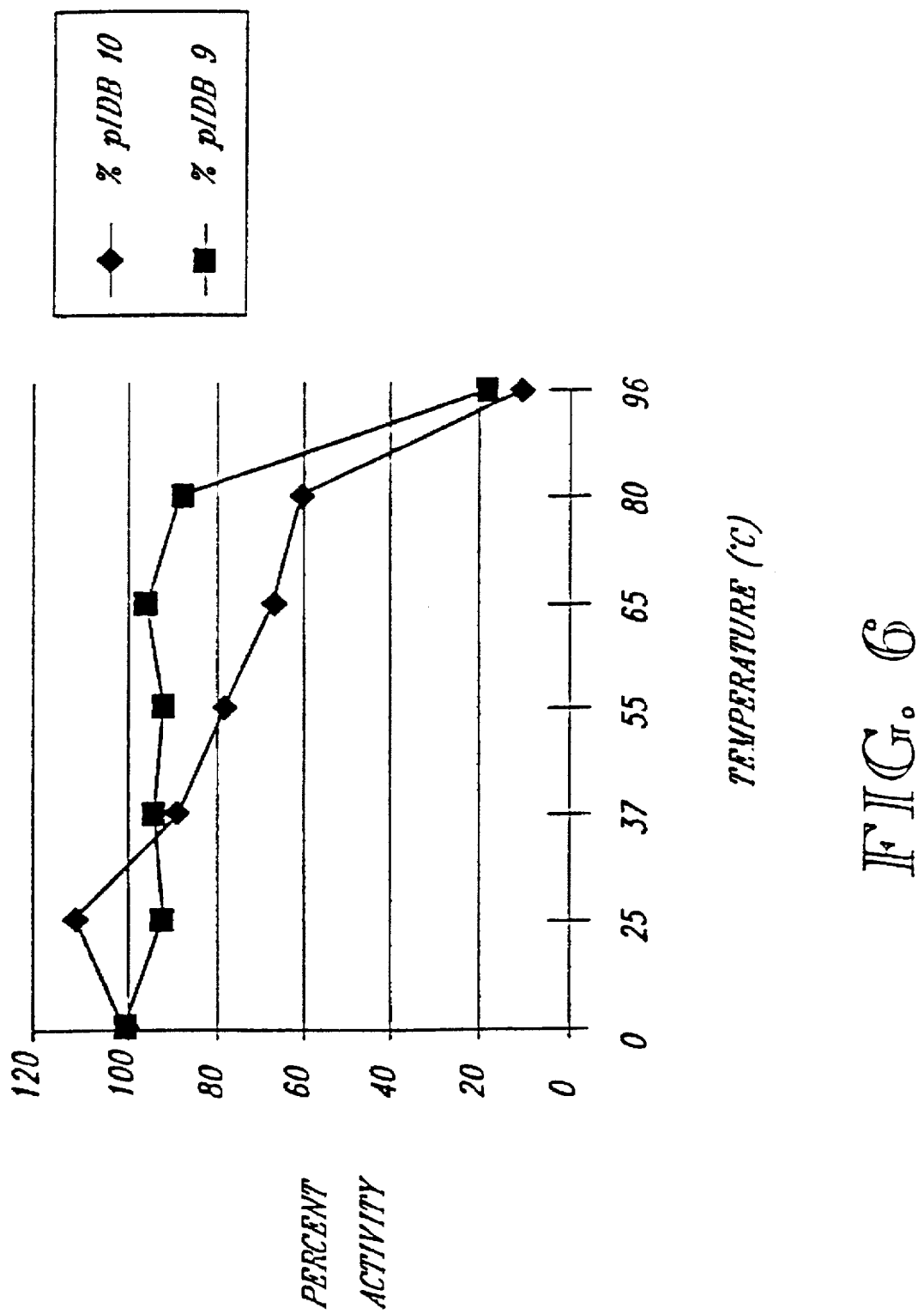
FIG. 6 is a graph which shows the effect of temperature on activity of native (pIDB9) or fusion (pIDB10) RNase H enzymes. The native (0.02 ng) and fusion (0.1 ng) enzymes were exposed for 10 min. to temperatures ranging from 0° to 96° C., followed by the acid soluble counts assay.
Figure 7A:
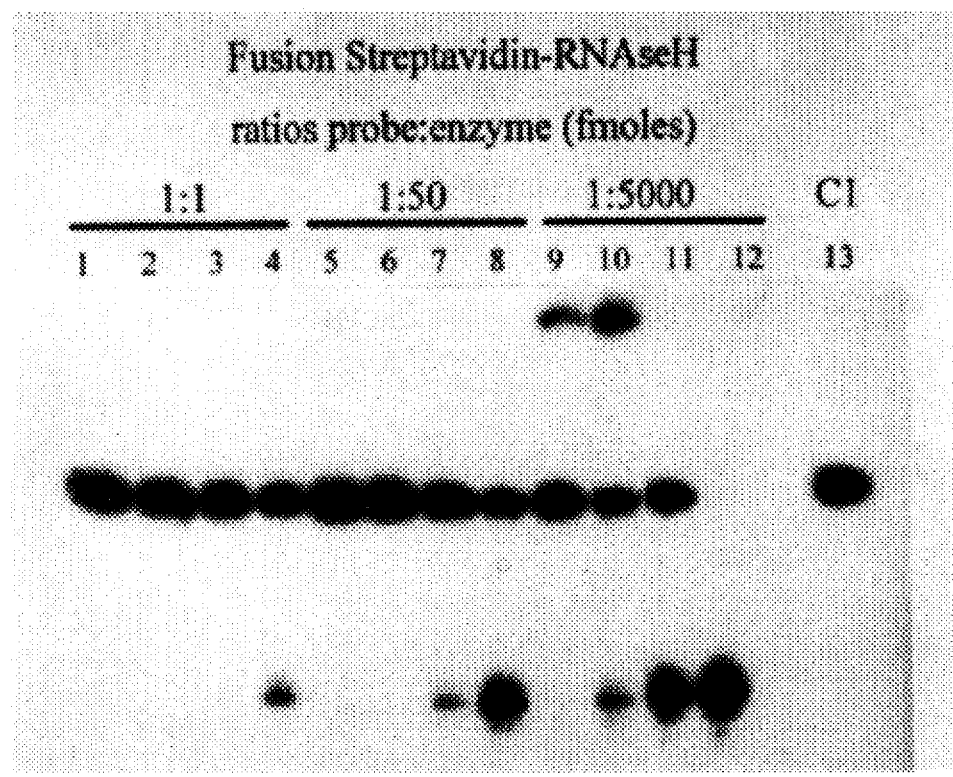
FIGS. 7A and 7B are autoradiograms of the results of an experiment comparing the activity of fusion (pIDB10, FIG. 7A) to the native RNase H (pIDB9, FIG. 7B) enzymes using ARK2B probe and ratios of probe to enzyme at: 1:1, 1:50 and 1:5000. The autoradiogram shows the substrate (uncleaved probe, upper band) and the product fragments (cleaved probe, lower band). Lanes 1, 5, and 9 are controls (probe and enzyme only); Lane 13 is also a control, (probe only); Lanes 2, 6 and 10 contain probe and enzyme with 0.01 fmole of target. Lanes 3, 7 and 11 contain probe and enzyme with 0.1 fmole of target. Lanes 4, 8 and 12 contain probe and enzyme with 1.0 fmole of target.
Figure 7B:
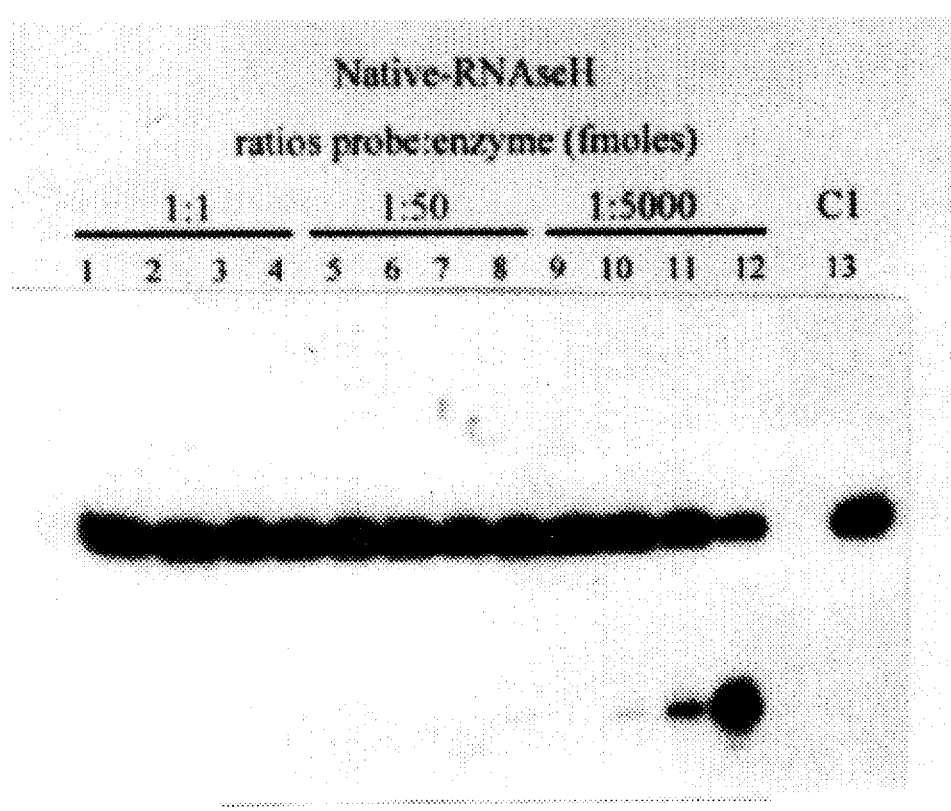

The RNase H activity of the fusion (pIDB10, pIDB11) was compared to the activity of the native RNase H (pIDB9). The results show that the native enzyme has approximately 8 fold greater activity than the fusion enzyme pIDB10. A preliminary experiment showed that the fusion enzyme pIDB10 is slightly more active than the fusion enzyme pIDB11. A temperature study was also performed to compare the fusion enzyme pIDB10 to the native enzyme pIDB9. Briefly, the enzymes were diluted in glycerol buffer (40% glycerol, sodium acetate 20 mM, pH 5.5, sodium chloride 150 mM) and subjected to different temperatures. As shown in FIG. 6, the native enzyme is more stable than the fusion, but the fusion enzyme is still active after 10 minutes of heat treatment (60% of control, i.e., no heat treatment).

Example 3

ATTACHMENT AND PURIFICATION OF THE BIOTINYLATED FLANKING SEQUENCE STREPTAVIDIN-RNASE H MOLECULE

Streptavidin-RNase H and a biotinylated oligonucleotide probe are mixed at a ratio of 1:5 (molar ratio of enzyme to probe). The sample is then separated by High Performance Liquid Chromatography (HPLC) on a NucleoPac PA 100 column (Dionex Corp., Sunnyvale, Calif.), utilizing a gradient of 100% Eluent 1 (20 mM Phosphate, pH 6.0) to 100% Eluent 2 (20 mM Phosphate/1.0M NACl, pH 6.0), at a flow rate of 1.5 ml/min.

Example 4

USE OF FUSION STREPTAVIDIN-RNASE H AND NUCLEIC ACID PROBES IN CYCLING REACTION

The fusion streptavidin-RNase H (pIDB10, fusion) was compared to the native enzyme (pIDB9) using biotinylated and non-biotinylated probes in a cycling reaction (see Example No. 5 for details on labeling of probes and cycling reaction conditions). A non-biotinylated probe, ARK2, 5'-GTCGTCAGAC CCaaaaCCCC GAGAGGG-3' (Sequence ID No. 13) and a biotinylated probe, ARK2B (ARK2L$_{12}$B) which has the identical nucleotide sequence as ARK2 but in addition has a biotin (B) and a spacer (L$_n$) at the 3' end, 5'-GTCGTCAGAC CCaaaaCCCC GAGAGGG-S$_{12}$-B-3' (Sequence ID No. 13), where each S is a 9 carbon linker, labeled with radioactive $^{32}$P-ATP at the 5' (see Example 5 for details). The synthetic target used in this experiment was the oligonucleotide complementary to the ARK2 probe. One fmole of fusion enzyme and 1 fmole of the native enzyme correspond to a dry weight of ≈0.03 ng and ≈0.02 ng, respectively.

In the initial experiment, different amounts of the enzymes were incubated in the reaction buffer with 1 fmole of the biotinylated probe, ARK2B, to give a final probe:enzyme ratio of 1:1, 1:50 or 1:5000. Results indicated that at a ratio of probe:enzyme of 1:1 and 1 fmole of target, the fusion enzyme was active while the native enzyme was not (FIG. 9, Table 2). At a ratio 1:50, both enzymes were active with 1 fmole of target, however, only the fusion enzyme was still active at 0.1 or 0.01 fmole of target. Both enzymes were active at a ratio of 1:5000. Using arbitrary units [CPT™ coefficient=% product/(target×probe×enzyme)], the fusion enzyme was shown to be at least 200 times more active than the native with the conditions used (Table 2). The streptavidin-RNase H fusion enzyme is more efficient than the native enzyme due to the streptavidin-RNase H binding to the probe through biotin, thereby ensuring efficient cleavage of each probe upon hybridization to the target.

Figure 8A:
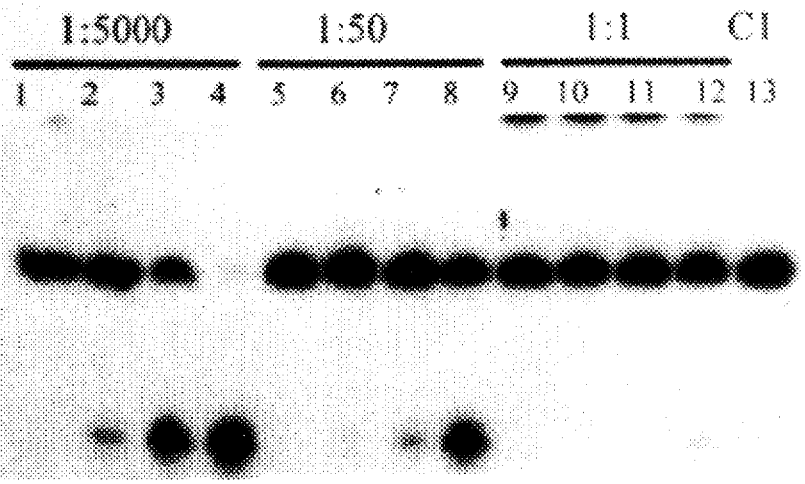
FIGS. 8A and 8B are autoradiograms of an experiment comparing ARK2B (biotinylated ARK2, FIG. 8A) and ARK2 (FIG. 8B) probes with the fusion enzyme (pIDB10) and using probe to enzyme ratios at: 1:1, 1:50 and 1:5000. The autoradiogram shows the substrate (uncleaved probe, upper band) and the product fragments (cleaved probe, lower band). Lanes 1, 5, and 9 are controls (probe and enzyme only); Lane 13 is also a control, (probe only); Lanes 2, 6 and 10 contain probe and enzyme with 0.01 fmole of target. Lanes 3, 7 and 11 contain probe and enzyme with 0.1 fmole of target. Lanes 4, 8 and 12 contain probe and enzyme with 1.0 fmole of target.
Figure 8B:
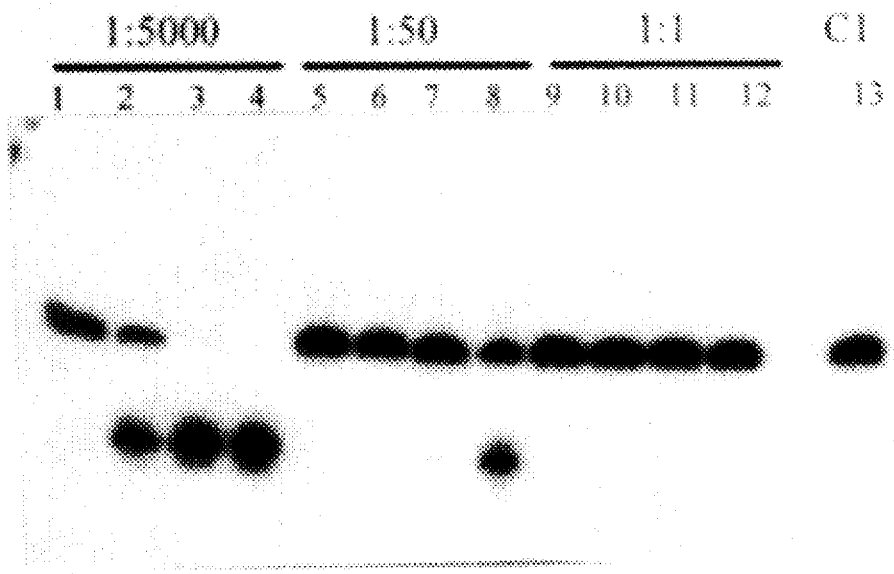

In order to verify the above, non-biotinylated (ARK2) and biotinylated (ARK2B) probes were compared using the fusion enzyme and the complementary target. The fusion enzyme was found to be active with ARK2B but not with ARK2 at probe to enzyme ratio of 1:1 and 1 fmole of target. Moreover, at a probe:enzyme ratio of 1:50, the fusion molecule was more active with ARK2B than ARK2 (FIG. 8). This experiment demonstrated that the fusion enzyme gave greater signal with the biotinylated probe than the non-biotinylated probe.

Example 5

USE OF ADJACENT SEQUENCE-ENZYME MOLECULES AND NUCLEIC ACID PROBE IN A CYCLING REACTION

A. Radioactive labeling of probe

The reaction probe is prepared by the addition of a radioactive $^{32}$P label to the 5' end of the oligonucleotide probe (Sambrook et al. 1990). Briefly, approximately 5 pmoles of the probe is labeled with 25 µL of [c-$^{32}$P]-ATP (6000 Ci/mmol) in a tube containing T4 polynucleotide kinase ("Ready to Go" Pharmacia cat. No. 27-0736-02) in a final volume of 50 µL and the reaction is incubated at 37° C. for 0.5 hour. Subsequently, 4 µL of 0.5M EDTA, pH 8.0 is added, and the reaction is further incubated at 90° C. for 5 minutes.

Labeled probe is separated from unincorporated label on 2 x 1 mL Sephadex G-50 column or 1 x Chromaspin-10 column (Clontech PT1300-1). The reaction mixture is first diluted to 100 µl with distilled water and then applied to the column. The reaction mixture is washed into the column with 400 µL of water. The labeled probe is then eluted with 400 µL of water, dried in a vacuum evaporator, and resuspended to (10 pmol) 1 fmole/µL in water.

B. Cycling reaction

Reaction tubes are set up in a final volume of 10 µl cycling buffer (40 mM Tris, pH 7.8, 8 mM MgCl$_2$, 0.025% Triton-X 100), containing 1 µl of target DNA (single or double stranded) sample, or with no DNA as a control, 1 µl (1 fmole) of labeled probe (or RNase H covalently linked to the probe, or fusion RNase H bound to biotinylated probe), 1 µl of the RNase H (0.1 ug @ 5000 fmole, or the adjacent oligonucleotide covalently linked to RNase H or the biotinylated adjacent oligonucleotide bound to fusion RNase H. An initial step is required for the use of fusion streptavidin-RNase H prior to the CPT™ reaction. The binding of fusion enzyme to biotinylated oligonucleotide probe or adjacent oligonucleotide is carried out for 15 min. using the cycling buffer supplemented with 1.0M NaCl. The tubes are incubated for 30 minutes at 65° C. for cycling, a temperature that allows efficient hybridization of the full-length probe (or adjacent oligonucleotides) to target (or adjacent to target) DNA sequences, but is above the T$_m$ of the duplex containing nicked probe, such that nicked probe melts off. Digested probe accumulates as RNase H and nucleic acid target catalyze the cleavage of the labeled probe. The target sequence remains intact and becomes available for further hybridization with uncleaved probe.

Following incubation, 10 μL of a dye mixture containing 10M urea, 0.01% bromphenol blue ("BPB"), 0.01% xylene cyanol and 50 mM EDTA is added to each reaction. Samples are then heated to 90° C. for 5 minutes to ensure denaturation, loaded onto a 7M urea-20% acrylamide/bis-acrylamide (19:1) gel, and electrophoresed at 450–600 volts.

The gel is analyzed on a PHOSPHORIMAGER™ utilizing IMAGEQUANT™ software (Molecular Dynamics, Sunnyvale, Calif.).

Example 6

USE OF FUSION STREPTAVIDIN-RNASE H FOR DETECTION OF VIRAL RNA OR MRNA IN CYCLING PROBE REACTION

An oligonucleotide primer sequence complementary to a sequence which is downstream from the mRNA or viral RNA target sequence is prepared with an internal biotin or biotin at the 5' end and used to prime a reverse transcriptase reaction. Streptavidin-RNase H fusion enzyme is added after the production of the biotinylated cDNA. A scissile oligonucleotide probe, which is complementary to the cDNA "target" sequence is added and a cycling reaction begins. Upon hybridization of the probe the RNase H cleaves the scissile linkage and the resulting oligonucleotide fragments will no longer be capable of remaining hybridized to the "target" cDNA. The detection of the cut probe is then performed after separation from uncut probe. Alternatively, an SH-group instead of biotin is utilized to covalently link the RNase H to the primer, followed by reverse transcriptase reaction and a cycling reaction.

The preparation of biotinylated oligonucleotide has been described above. Briefly, the first strand of cDNA is synthesized in a standard 50 μl reaction containing 20 μg total RNA, 50 mM Tris-HCl pH 8.3, 75 mM KCl, 10 mM dithiothreitol (DTT), 3 mM $MgCl_2$, 1 mM of each dNTP (Pharmacia), 200 pmoles biotinylated oligonucleotide, 2.5 μg BSA (nuclease free, Pharmacia) 10 U human placental RNase inhibitor and 600 units of MMLV reverse transcriptase (BRL-Life technologies). The reaction is incubated for 1 h at 37° C., after which samples are phenol-chloroform extracted and precipitated with ethanol (Sambrook et al. 1990). The synthesis of cDNA is quantified by measuring counts incorporated into acid-precipitable material in an identical parallel reaction containing 2.5 μCi of [$\alpha$-$^{32}$P] dCTP (3000 Ci/mmol, Dupont-NEN). A cycling reaction may then be carried out as described in Example 5.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

---

We claim:

1. An oligonucleotide-enzyme molecule, comprising an enzyme capable of cleaving scissile linkages and an oligonucleotide having the structure [(NA$_1$)$_x$ (—S—)$_z$ (—NA$_2$)$_y$]$_n$ wherein NA$_1$ and NA$_2$ are nucleic acid sequences, S is a scissile linkage and x, y and z are integers from 1–100 and n is an integer from 1–10.

2. The oligonucleotide-enzyme molecule of claim 1 wherein said enzyme is an *E. coli* RNase H.

3. The oligonucleotide-enzyme molecule of claim 1 wherein said enzyme is a thermophilic RNase H.

4. The oligonucleotide-enzyme molecule of claim 1 wherein NA$_1$ is selected from the group consisting of DNA and RNA.

5. The oligonucleotide-enzyme molecule of claim 1 wherein NA$_2$ is selected from the group consisting of DNA and RNA.

6. The oligonucleotide-enzyme molecule of claim 1 wherein S is selected from the group consisting of DNA and RNA.

7. The oligonucleotide-enzyme molecule of claim 1 wherein NA$_1$ and NA$_2$ are DNA molecules, —S— is a RNA molecule and the enzyme is RNase H.

8. The oligonucleotide-enzyme molecule of claim 1 wherein said enzyme is fused to an avidin or streptavidin binding fragment and the oligonucleotide is covalently attached to a biotin.

9. The oligonucleotide-enzyme molecule of claim 1 wherein said enzyme is covalently attached to the oligonucleotide through a linker molecule.

10. The oligonucleotide-enzyme molecule of claim 9 wherein the linker molecule has the structure $L_n$, wherein L is a monomeric unit, and n is between 1 and 200.

11. The oligonucleotide-enzyme molecule of claim 10 wherein said linker molecule is a heterobifunctional linker.

12. The oligonucleotide-enzyme molecule of claim 11 wherein the heterobifunctional linker is succinimidyl 4-(N-maleimidomethyl) cyclohexane-1-carboxylate.

13. A method of detecting a target nucleic acid molecule, comprising:
   (a) reacting a target nucleic acid molecule and a complementary single-stranded nucleic acid probe having a scissile linkage and an attached enzyme molecule, under conditions which allow the target nucleic acid and probe to hybridize to each other and form a double-stranded, target-probe complex, wherein the enzyme molecule is capable of cleaving the probe of the target-probe complex at the scissile linkage, such that one or more portions of the nucleic acid probe are released from the target-probe-adjacent sequence complex; and
   (b) detecting the released portions of the nucleic acid probe, and thereby determining the presence of the target nucleic acid.

14. A method of detecting a target nucleic acid molecule, comprising:
   (a) reacting a target nucleic acid molecule, a complementary single-stranded nucleic acid probe having a scissile linkage, and a first complementary adjacent sequence-enzyme molecule under conditions which allow the probe and adjacent sequence-enzyme molecule to hybridize to the target nucleic acid and form a double-stranded, target-probe adjacent sequence complex, wherein the adjacent sequence-enzyme molecule is capable of cleaving the probe at the scissile linkage, such that one or more portions of the nucleic acid probe are released from the target-probe adjacent sequence complex; and
   (b) detecting the released portions of the nucleic acid probe, and thereby determining the presence of the target nucleic acid.

15. The method according to claims 13 or 14 wherein said enzyme is an *E. coli* RNase H.

16. The method according to claims 13 or 14 wherein said enzyme is a thermophilic RNase H.

17. The method according to claims 13 or 14 wherein said single-stranded nucleic acid probe has the structure $[(NA_1)_x (—S—)_z (—NA_2)_y]_n$, wherein $NA_1$ and $NA_2$ are nucleic acid sequences, S is a scissile linkage and x, y and z are integers from 1–100 and n is an integer from 1–10.

18. The method according to claim 17 wherein $NA_1$ is selected from the group consisting of DNA and RNA.

19. The method according to claim 17 wherein $NA_2$ is selected from the group consisting of DNA and RNA.

20. The method according to claim 17 wherein S is selected from the group consisting of DNA and RNA.

21. The method according to claim 17 wherein $NA_1$ and $NA_2$ are DNA molecules, —S— is a RNA molecule and the enzyme is RNase H.

* * * * *